United States Patent
Qin et al.

(10) Patent No.: US 11,402,362 B2
(45) Date of Patent: Aug. 2, 2022

(54) STEREOSCOPIC MONITORING AND DATA MINING SYSTEM AND METHOD FOR HARMFUL LAKE CYANOBACTERIA BLOOM

(71) Applicant: NANJING INSTITUTE OF GEOGRAPHY & LIMNOLOGY. CHINESE ACADEMY OF SCIENCES, Nanjing (CN)

(72) Inventors: Boqiang Qin, Nanjing (CN); Tingfeng Wu, Nanjing (CN); Guangwei Zhu, Nanjing (CN); Yunlin Zhang, Nanjing (CN); Wei Li, Nanjing (CN)

(73) Assignee: NANJING INSTITUTE OF GEOGRAPHY, Nanjing (CN)

( * ) Notice: Subject to any disclaimer, the term of this patent is extended or adjusted under 35 U.S.C. 154(b) by 629 days.

(21) Appl. No.: 16/329,943

(22) PCT Filed: Jun. 19, 2017

(86) PCT No.: PCT/CN2017/089012
§ 371 (c)(1),
(2) Date: Mar. 1, 2019

(87) PCT Pub. No.: WO2018/214190
PCT Pub. Date: Nov. 29, 2018

(65) Prior Publication Data
US 2021/0293770 A1    Sep. 23, 2021

(51) Int. Cl.
*G01N 33/18* (2006.01)
*G01D 21/02* (2006.01)
*G01N 33/00* (2006.01)

(52) U.S. Cl.
CPC ............. *G01N 33/18* (2013.01); *G01D 21/02* (2013.01); *G01N 33/0098* (2013.01)

(58) Field of Classification Search
CPC ..... G01N 33/18; G01N 33/0098; G01D 21/02
(Continued)

(56) References Cited

U.S. PATENT DOCUMENTS

| 6,536,272 B1 * | 3/2003 | Houston | G01N 1/12 702/2 |
| 7,027,149 B2 * | 4/2006 | O'Mongain | G01N 21/31 356/300 |
| 2012/0058542 A1 * | 3/2012 | Wu | A01K 61/50 435/257.1 |

FOREIGN PATENT DOCUMENTS

CN       103604423     *  2/2014

* cited by examiner

*Primary Examiner* — Robert R Raevis
(74) *Attorney, Agent, or Firm* — PROI Intellectual Property US; Klaus Michael Schmid (57) ABSTRACT

The invention relates to a comprehensive monitoring and data mining system and method for algae bloom of lake, wherein, the method comprises acquiring monitoring indicator data related to algae bloom of lake by three ways, i.e., remote sensing monitoring, automatic monitoring and manual surveying, and transmitting the acquired data to a data center by Internet; performing data backup and data preprocessing of the received data in the data center, including temporal interpolation, spatial interpolation and outlier determination and processing; transmitting the preprocessed data to a database for storage; performing computation of 3D numerical model of lake according to the data source stored in the database, assessing the risk of algae bloom of the lake to be monitored according to the simulation data of the numerical model, and displaying predictive warning information on algae bloom of the lake on a public platform.

9 Claims, 2 Drawing Sheets

(58) Field of Classification Search
USPC ....... 73/61.43, 53.01, 866; 435/257.1–257.6; 702/19
See application file for complete search history.

STEREOSCOPIC MONITORING AND DATA MINING SYSTEM AND METHOD FOR HARMFUL LAKE CYANOBACTERIA BLOOM

TECHNICAL FIELD

The invention belongs to the technical field of environmental monitoring and assessment and data mining, in particular relates to a comprehensive monitoring and data mining system and method for algae bloom of lake.

BACKGROUND

A common phenomenon caused by eutrophication of lakes is that, under suitable hydro-meteorological conditions, many phytoplanktons, especially the algae with buoyancy or motor ability, will proliferate abnormally and aggregate to form algae blooms, thus causing a series of serious ecological and environmental problems, including the reduced of water transparency, declined of DO, death of aquatic animals and plants, water odor, decreased of biodiversity, and damages to human health through the food chain. The ecological disasters caused by eutrophication and abnormal proliferation of cyanobacteria have posed a huge threat to the ecological health and sustainable development of many famous lake ecosystems, including Lake Erie in United States, Lake Winnipeg in Canada, Baltic Sea in Europe, Lake Victoria in Africa and Lake Biwa in Japan. Although the algae bloom of the lake is serious, there has no way to solve this problem thoroughly for the moment. Under this premise, the well monitoring and prevention of algae blooms is the key to alleviating this ecological disaster and reducing social and economic losses.

At present, there have been many research reports on technical methods for monitoring cyanobacteria. "MODIS satellite high-precision monitoring method for cyanobacteria blooms of large-scale shallow lake" proposed in Chinese patent application 201410023795.8 uses a remote sensing technique to monitor cyanobacteria blooms. Without effect of cloud coverage, this method can only provide data once a day. In the event of cloud coverage, it cannot provide valid data. However, research has shown that the formation and disappearance of blooms can only remain a few hours. But it is obvious that the sampling frequency of the remote sensing technique cannot accurately reflect the rapid dynamic real-time changes of water blooms. Similarly, though the real-time monitoring of "buoys for cyanobacteria monitoring" proposed by Chinese patent application 201020219363.1 can record the change process of environmental factors related to algae blooms with high temporal resolution, this technique can only provide water environment information of the point where the equipment is located, and it is obvious that it cannot record surface information of cyanobacteria blooms that is highly differentiated in space. Yang Hongwei et al. disclosed a "Taihu cyanobacteria bloom warning platform based on Internet of Things technique". The platform based on multi-source data can predict probability of occurrence of cyanobacteria bloom warning in three-day advance according to the four-layer connotation design of the Internet of Things, and publish information by Internet; but from its design framework and text description, the main problems of this technique lay in that: (1) it does not include satellite receiving antenna, the acquired data are not real-time satellite remote sensing data, so the platform cannot realize the function of automatic real-time acquisition of satellite remote sensing data; (2) the automatic monitoring station only describes the setting of the chlorophyll sensor in detail, does not mention the monitoring indicators, arrangement form and parameter settings of other instruments and equipment, and does not introduce real-time monitoring, power supply and safety functions; (3) the technique only mentions the cyanobacteria biomass model, and has no simulation function of the ecological process closely related to the algae life process, such as nutrient salt circulation, sediment erosion and suspension and dissolved oxygen dynamics; and (4) the technique also has the disadvantage of not fully exploiting the value of the data generated by the monitoring. Both remote sensing and automatic monitoring can generate massive data of algae blooms. In conclusion, the prior art can neither fully utilize the data to serve lake research and management, nor provide valuable and readable algae bloom information to the public. Therefore, in order to acquire algae bloom information more timely and accurately, and to fully increase the value of the information, it needs measurement and control system to acquire the spatial-temporal continuous data related to cyanobacteria, and some high-efficiency data analysis and processing techniques and methods, including statistical analysis of data, data assimilation, model prediction, real-time correction of parameters, disaster assessment and disaster information publishing. Only establishing comprehensive monitoring and data mining systems and methods for algae blooms can meet the needs of economic and social development and ecological environmental protection for algae bloom monitoring and prevention.

SUMMARY OF THE INVENTION

The invention is to overcome the disadvantages of the prior art and provide a comprehensive monitoring and data mining system for algae bloom of lake. With the system and method provided by the present invention to address the problem of great spatial and temporal changes of cyanobacteria blooms in lakes, the real-time algae bloom data are collected by integrating satellite remote sensing, automatic monitoring and manual surveying techniques, database, data assimilation and numerical model are used to perform data mining, achieve automatic, real-time and accurate collection, processing and extraction of algae bloom information, and provide valuable and highly recognizable monitoring and prevention information for rapid, timely and accurate response to algae blooms, so as to ultimately minimize socio-economic and ecological environment losses caused by the disasters.

For the above technical purposes, the present invention adopts the following technical scheme:

A comprehensive monitoring and data mining system for algae bloom of lake, comprising a monitoring system and a data processing system;

Monitoring system is used for acquiring data to be monitored; Monitoring system comprises a remote sensing monitoring system for monitoring by remote sensing, an automatic monitoring system for monitoring by automatic monitoring and a manual surveying system for manual acquisition of data to be monitored;

Remote sensing monitoring system comprises a satellite data receiving antenna, a computer and a power supply system, wherein the power supply system is used to supply power for power consuming devices, the satellite data receiving antenna receives satellite data and transmits them to the computer, the data are subject to remote sensing inversion by the computer and the processed data are transmitted to the data processing system by Internet;

Automatic monitoring system is a monitoring network formed by a plurality of automatic monitoring stations via wireless network, and a single automatic monitoring station consists of a water surface supporting system, a power supply system, a safety warning system and a data acquisition system; Water surface supporting system is a bearing structure for hardware devices of the automatic monitoring station; Power supply system is used to supply power for power consuming devices of the automatic monitoring station; Safety warning system is used for safety warning and preventing the automatic monitoring station from accidental damages; and data acquisition system is used to acquire data to be monitored from a meteorological instrument, a hydrological instrument, a water-quality instrument and a video instrument and transmit the acquired data to the data processing system via wireless network.

The water surface supporting system is bearing structure of the whole system, and it can be a buoy body, a trestle bridge or a water platform. The supporting system has an upper portion above the water surface, and a lower portion fixed at the bottom of the lake, and functions to support the whole system structure. The power supply system is fixed on the water surface supporting system and supplies power for other power consuming devices through cables. The safety warning system is fixed on the water surface supporting system and includes beacon lights, fluorescent bands and warning signs, etc.

Manual surveying system acquires data manually and transmits the data to the data processing system by Internet;

Data processing system is used to receive and process the data acquired by the monitoring system; The data processing system comprises a server, an array processor, a computer, a computing workstation, a hardware firewall, a router, network cables and a power supply device; The server adopts a dual-unit hot-standby mode, two servers and the array processor for data storage realize heartbeat connection through a three-prong cable, all computers, servers, and computing workstations are connected to the hardware firewall through a network cable, and the hardware firewall is communicated to the external network through the router.

In the present invention, the server adopts a dual-unit hot-standby mode, and the central server is installed as two servers that are mutually backed up, and only one server runs at a time. When one of servers fails to start, the other backup server will start and run quickly and automatically. The computing workstation is mainly used for computing of 3D numerical models. The hardware firewall is mainly used to protect the whole system from attacks, and the router provides network services for the whole system. These devices described above will be placed in the cabinet and the power supply of the cabinet will be connected to the uninterruptible power supply. Normally, all devices are powered by an external power supply. When the external power supply is interrupted unexpectedly, the whole system is powered by the uninterruptible power supply.

After receiving the data, the data processing system performs data backup and data processing of the received data, acquires predictive indicators and risk assessments of algae bloom of the lake, and publishes them through a public platform.

The invention further provides a comprehensive monitoring and data mining method for algae bloom, specifically comprising the steps as follows:

(1) Acquiring monitoring indicator data related to algae bloom of the lake to be monitored by three ways, i.e., remote sensing monitoring, automatic monitoring and manual surveying, wherein the monitoring indicator data comprise meteorological indicators, hydrological indicators, water-quality indicators and video images, and transmitting the acquired data to a data center by Internet.

Wherein, the remote sensing monitoring refers to a real-time monitoring by remote sensing; The remote sensing monitoring data acquisition refers to receiving satellite signals by the satellite receiving antenna and transmitting to the remote sensing processing computer, and the satellite data inversion software generates various remote sensing indicators, thereafter the data are sent to the data center of the server by the computer sharing function in the local area network.

Automatic monitoring refers to a monitoring network formed by a plurality of automatic monitoring stations via a wireless network to monitor the indicators to be monitored; The automatic monitoring comprises collecting meteorological, hydrological and water quality indicators and videos through various types of sensors configured, sending them to the data center of the server over a commercial communication network, and receiving data by a commercial software installed on server side.

Manual surveying refers to a manual survey of the indicators; the manual surveying refers to on-site data and water sample acquisition through preset monitoring sites within a specified time, and sending the water samples to a laboratory to detect relevant indicators, and the manual surveying data are manually uploaded to the data center of the server via a web site.

The remote sensing monitoring, automatic monitoring and manual surveying data transmitted to the server are stored in the data center of the server by specific file naming to facilitate identification of the original data by various data processing programs.

Wherein, the indicator system applicable for the remote sensing is determined in the way that, based on the effect of water quality indicators such as water temperature and water color on the emission and absorption spectra of optical sensors carried by the satellite, the water quality indicators which are not only closely related to algae blooms but also adopted to extract valid information from spectral signals by inversion algorithms are selected as satellite inversion indicators, including water temperature, transparency, suspended substance (SS), chlorophyll a, area of cyanobacteria bloom and intensity, etc. Remote sensing monitoring has a temporal resolution within one day, and a spatial resolution within 1 km.

The indicator system applicable for the automatic sensing is determined in the way that, based on research on technique maturity of meteorological, hydrological and water quality sensors on the market, the indicators which are not only closely related to algae blooms but also supported by sensor techniques with high maturity are selected as automatic monitoring indicators, including meteorological indicators (wind speed, wind direction, atmospheric pressure, temperature, humidity, solar radiation and rainfall, etc.); Hydrological indicators (3D flow profile, water depth, effective wave height and period, etc.); Water quality indicators (water temperature, dissolved oxygen, turbidity, conductivity, redox potential, phycocyanobilin, chlorophyll, etc.); Video images.

The indicator system applicable for the manual surveying is determined such that indicators closely related to algae blooms other than those of remote sensing inversion and automatic monitoring are acquired by manual surveying, including total nitrogen, total dissolved nitrogen, ammonia nitrogen, nitrate nitrogen, nitrite nitrogen, total phosphorus, total dissolved phosphorus, orthophosphate and other cyanobacteria-derived pollutants.

The remote sensing monitoring, automatic monitoring and manual surveying data are stored in the data center of the server by specific file naming to facilitate identification of the original data by various data processing programs.

(2) Performing data backup and data preprocessing of the received data in the data center, wherein said data preprocessing includes the steps as follows:

Checking the data according to the set time interval for data acquisition, and performing data interpolation by a temporal interpolation if the data are interrupted.

Filling the missing data of a cloud coverage area by a spatial interpolation for satellite data acquired by the remote sensing monitoring.

Performing an outlier determination and processing of the data, and replacing the abnormal data with the data before them.

Transmitting the preprocessed data along with the raw data received by the data center to database for storage.

(3) Constructing a 3D numerical model of the lake to be monitored according to the data source stored in the database, as follows:

Constructing a hydrodynamic model of the lake to be monitored.

Superimposing a material migration and transformation model on the hydrodynamic model of the lake to be monitored, and performing equation coupling computation of the two models; wherein, said material migration and transformation model has such computation scalars as illumination, suspended substance, algae growth, nutrient salt circulation and dissolved oxygen.

Solving the model by the finite difference method to acquire simulation data of the numerical model.

The 3D numerical model used may be the existing models such as FVCOM, ELCOM-CAEDYM, and EFDC, or a model self-developed based on the theory of environmental fluid mechanics.

(4) Assessing the risk of algae bloom of the lake to be monitored according to the simulation data of the numerical model, wherein, the risk assessments of disasters can be achieved by existing mature algorithms.

(5) Displaying predictive warning information on algae bloom of the lake on a public platform.

In the method of the invention, further, in said step (2), the data are classified and stored in the database as follows:

For single-point temporal continuous data, all data of a single monitoring station are stored in a single data sheet;

2D data are directly stored in the data sheet.

The data generated by the 3D numerical model are stored in the data sheet by time node;

Image or video data are stored in an array processor, and a data sheet is created in the database to record the path of image or video, the fields include number, time, and image/video path, and the image or video data are accessed in an indexed manner. The remote sensing monitoring, automatic monitoring and manual surveying data are stored in the data center of the server by specific file naming to facilitate identification of the original data by various data processing programs.

Wherein, the database is constructed for multi-source heterogeneous data sets. A commercial software such as Microsoft SQL Server, Access, and Oracle is used, preferably, Oracle.

In the method of the invention, in said step (2), said temporal interpolation method employs linear interpolation, spline function interpolation or piecewise interpolation.

The spatial interpolation method employs the proximal point method, the Kriging method or the inverse distance weighted interpolation method.

The basis for outlier determination and processing is trend test, expertise or numerical comparison.

Preferably, said temporal interpolation method employs linear interpolation, and the algorithm is as follows:

For the data $a_1$ and $a_2$ in the data set, in the chronological order, the data $b_1, b_2, \ldots, b_n$ are missing there between, then:

$$b_i = \frac{(a_2 - a_1) * i}{n} + a_1 \tag{1}$$

where i=[1, n].

Said spatial interpolation method employs the inverse distance weighted interpolation method, and the algorithm is as follows:

Assuming that the indicator values at the spatial point coordinates $(x_0, y_0)$ miss $C(x_0, y_0)$, a search radius is set such that there are at least 3 data points within the radius; then the data of these known data points are used to obtain indicator values of unknown points:

$$C(x_0, y_0) = \frac{\frac{C(x_1, y_1)}{d_1} + \frac{C(x_2, y_2)}{d_2} + \ldots + \frac{C(x_n, y_n)}{d_n}}{\frac{1}{d_1} + \frac{1}{d_2} + \ldots + \frac{1}{d_n}} \tag{2}$$

Where, $C(x_1, y_1)$, $C(x_2, y_2)$, ..., $C(x_n, y_n)$ respectively represent the measured indicator values at the coordinate points in parentheses; $d_1, d_2, \ldots, d_n$ respectively represent the straight-line distances from the coordinate points in parentheses to the spatial point coordinates $(x_0, y_0)$, n≥3.

The outlier determination is performed by the 5× variance method as follows: computing the mean and variance of the $m^{th}$ measured datum $a_m$ and the five data before and after it.

$$\bar{a} = \frac{1}{11}\Sigma_{n=1}^{11} a_n \tag{3}$$

$$SD^2 = \frac{1}{10}\Sigma_{n=1}^{11}(a_n - \bar{a})^2 \tag{4}$$

With $\bar{a} \pm 5$ SD as the judgment interval, the data satisfying $\bar{a}-5$ SD$\leq a_m \leq \bar{a}+5$ SD are routine data, otherwise $a_m$ is replaced by the $m-1^{th}$ datum.

In the method of the invention, the 3D numerical model used in said step (3) may be the existing models such as FVCOM, ELCOM-CAEDYM, and EFDC, or a model self-developed based on the theory of environmental fluid mechanics; and the invention preferably provides a self-developed model as follows:

The control equation of the hydrodynamic model is as follows:

$$\frac{\partial Hu}{\partial x} + \frac{\partial Hv}{\partial y} + \frac{\partial Hw}{\partial \sigma} + \frac{\partial \xi}{\partial t} = 0 \tag{5}$$

$$\frac{\partial u}{\partial t} + u\frac{\partial u}{\partial x} + v\frac{\partial u}{\partial y} + w\frac{\partial u}{\partial \sigma} = \tag{6}$$

$$-fv - \frac{g\rho}{\rho_0}\frac{\partial \xi}{\partial x} + \frac{\partial}{\partial x}\left(A_h\frac{\partial u}{\partial x}\right) + \frac{\partial}{\partial y}\left(A_h\frac{\partial u}{\partial y}\right) + \frac{1}{H^2}\frac{\partial}{\partial \sigma}\left(A_v\frac{\partial u}{\partial \sigma}\right) + B_x$$

$$\frac{\partial v}{\partial t} + u\frac{\partial v}{\partial x} + v\frac{\partial v}{\partial y} + w\frac{\partial v}{\partial \sigma} = \quad (7)$$

$$-fu - \frac{g\rho}{\rho_0}\frac{\partial \xi}{\partial y} + \frac{\partial}{\partial x}\left(A_h\frac{\partial v}{\partial x}\right) + \frac{\partial}{\partial y}\left(A_h\frac{\partial v}{\partial y}\right) + \frac{1}{H^2}\frac{\partial}{\partial \sigma}\left(A_v\frac{\partial v}{\partial \sigma}\right) + B_y$$

$$\frac{1}{H}\left(\frac{\partial HT}{\partial t} + \frac{\partial HuT}{\partial x} + \frac{\partial HvT}{\partial y} + \frac{\partial HwT}{\partial \sigma}\right) = \quad (8)$$

$$\frac{\partial}{\partial x}\left(K_h\frac{\partial T}{\partial x}\right) + \frac{\partial}{\partial y}\left(K_h\frac{\partial T}{\partial y}\right) + \frac{1}{H^2}\frac{\partial}{\partial \sigma}\left(K_v\frac{\partial T}{\partial \sigma}\right) + \frac{S_h}{\rho C_P} + B_T$$

$$\rho(T) = 1000\left(1 - \frac{T+288.9414}{508929.2(T+68.12963)}(T-3.9863)^2\right) \quad (9)$$

Where, u, v and w are respectively the flow rates in three directions x, y, and σ; H and t are water depth and time; g and ξ are gravitational acceleration and water level; f is Coriolis force, P is pressure, $B_x$, $B_y$, and $B_T$ are respectively the minor terms introduced by coordinate transformation of x-direction momentum, y-direction momentum and temperature equation; T is temperature; $S_h$ is the heat entering the system from the outside; $C_p$ is the thermal capacity of water; $K_h$ and $K_v$ are the diffusion coefficients of heat in horizontal and vertical directions; ρ is water density, $\rho_0$ is water reference density; $A_h$ is horizontal eddy viscosity coefficient; $A_v$ is vertical eddy viscosity coefficient, which is defined by the formulas:

$$A_v = A_{v0}(1+m_0R_i)^{m_1} \quad (10)$$

$$A_{v0} = v_0 + \frac{l^2}{H}\sqrt{\left(\frac{\partial u}{\partial \sigma}\right)^2 + \left(\frac{\partial v}{\partial \sigma}\right)^2} \quad (11)$$

Where, $v_0$, $m_0$, $m_1$ values are respectively 5.0×10−6 m2/s, 0.1 and −1; l is Prandtl's length; $R_i$ is Richardson number, reflecting fluid stability condition, and its expression formula is:

$$R_i = -\frac{Hg}{\rho\left(\left(\frac{\partial u}{\partial \sigma}\right)^2 + \left(\frac{\partial v}{\partial \sigma}\right)^2\right)}\frac{\partial \rho}{\partial \sigma} \quad (12)$$

The wind energy input at the water-air interface with σ=1 and the friction resistance at the water-soil interface with σ=0 are expressed as:

$$\frac{\rho_S A_v}{H}\left(\frac{\partial u}{\partial \sigma}, \frac{\partial v}{\partial \sigma}\right) = (\tau_{Wx}, \tau_{Wx}) = \rho_a C_{WD}\sqrt{WS_x^2 + WS_y^2}(WS_x, WS_y) \quad (13)$$

$$\frac{A_v}{H}\left(\frac{\partial u}{\partial \sigma}, \frac{\partial v}{\partial \sigma}\right) = (\tau_{sx}, \tau_{sx}) = C_{SD}\sqrt{u^2+v^2}(u, v) \quad (14)$$

Where, $\rho_a$ and $\rho_s$ represent air density and surface water density, respectively; $C_{WD}$ is wind drag coefficient; WS is wind speed at 10 m above water meter; $C_{SD}$ is friction coefficient at the bottom of the lake.

The hydrodynamic equations (5), (6) and (7) are solved by the splitting operator technique to generate the internal and external modes; then the internal and external modes are discretized by the finite difference, wherein, the format of horizontal and temporal differences is explicit and the format of vertical difference is implicit, and the water surface displacement is subject to smoothing in temporal direction by a low-pass filter; and finally, the chasing method is used to solve the super-large sparse matrix.

The control equation of material migration and transformation model superimposed on the hydrodynamic model is as follows:

$$\gamma_{PAR}(I, J, K) = \gamma_{0,PAR} + \gamma_{1,PAR}CHLA(I, J, K) + \gamma_{2,PAR}SED(I, J, K) \quad (15)$$

$$\frac{\partial S}{\partial t} + u\frac{\partial S}{\partial x} + v\frac{\partial S}{\partial y} + \left(w - \frac{w_S}{H}\right)\frac{\partial S}{\partial \sigma} = \quad (16)$$

$$B_S + \frac{\partial}{\partial x}\left(D_h\frac{\partial S}{\partial x}\right) + \frac{\partial}{\partial y}\left(D_h\frac{\partial S}{\partial y}\right) + \frac{1}{H^2}\frac{\partial}{\partial \sigma}\left(D_v\frac{\partial S}{\partial \sigma}\right) + \frac{J_0}{H}$$

$$\frac{\partial C_i}{\partial C} + u\frac{\partial C_i}{\partial x} + v\frac{\partial C_i}{\partial y} + w\frac{\partial C_i}{\partial \sigma} = \quad (17)$$

$$B_c + \frac{\partial}{\partial x}\left(D_h\frac{\partial C_i}{\partial x}\right) + \frac{\partial}{\partial y}\left(D_h\frac{\partial C_i}{\partial y}\right) + \frac{1}{H^2}\frac{\partial}{\partial \sigma}\left(D_v\frac{\partial C_i}{\partial \sigma}\right) + SK_i$$

Where, $\gamma_{PAR}$(I, J, K) and $\gamma_{0,PAR}$ represent total attenuation coefficient and attenuation coefficient of pure water respectively; $\gamma_{1,PAR}$ and $\gamma_{2,PAR}$ represent specific attenuation coefficient of algae and specific attenuation coefficient of non-algae particulates; CHLA(I, J, K) is biomass of phytoplankton expressed by the concentration of chlorophyll a; SED(I, J, K) is the concentration of non-algae particulates; u, v and w are 3D the flow rates of new time step; S is the concentration of suspended substances; $w_s$ is the sedimentation rate of suspended substances; $J_0$ is the flux term at water-soil interface, including erosion flux and sedimentation flux; $C_i$ represents the concentration of the i$^{th}$ substance; $SK_i$ represents biochemical process items, with 1=1, 2, 3, 4, 5, representing chlorophyll a, zooplankton, available phosphorus, available nitrogen, dissolved oxygen, and five-day biochemical oxygen demand (BOD5.

Based on the computation results of the hydrodynamic model, the above equations are discretized by the finite difference method in a rectangular grid: the spatially discretizing is performed in upwind scheme; the format of horizontal and temporal differences is explicit and the format of vertical difference is implicit, and the chasing method is used to solve the super-large sparse matrix.

The biochemical term involved in equation (17) is computed by the following method:

For biochemical term of algae:

$$SK_1 = (\mu - \tau_{NP} \cdot KM)CHLA_{i,j,k}\frac{KS}{H\Delta Z}(CHLA_{i,j,k+1} - CHLA_{i,j,k})\tau_f - \quad (18)$$

$$ZOOP_{i,j,k}ZP \cdot CHLA_{i,j,k} \cdot \tau_p$$

where μ is the total growth rate; KM is the non-predation mortality; KS is the floating rate; ZP is the filter feeding rate of zooplankton; CHLAi, j and k represent the biomass of phytoplankton in the i, j and k grids; $\tau_a$, $\tau_f$ and $\tau_p$ here as well as $\tau_{ZP}$, $\tau_{KB}$, $\tau_s$, $\tau_d$ and $\tau_{so}$ involved in the formula below are all temperature influence factors, and their expression formulae are $\theta_a^{T-20}$, $\theta_f^{T-20}$, $\theta_p^{T-20}$, $\theta_{ZP}^{T-20}$, $\theta_{KB}^{T-20}$, $\theta_s^{T-20}$, $\theta_d^{T-20}$ and $\theta_{so}^{T-20}$ respectively, wherein, $\theta_a$, $\theta_p$, $\theta_{ZP}$, $\theta_{KB}$, $\theta_s$, $\theta_d$ and $\theta_{so}$ are temperature multipliers;

For biochemical term of zooplankton:

$$SK_2 = \left(\mu_{ZP} \cdot ZOOP \cdot \frac{CHLA}{KCHLA + CHLA} - BFISH \cdot FISH\right) \cdot \tau_{ZP} \quad (19)$$

where $\mu_{zp}$ is the growth rate of zooplankton; KCHLA is the predation semisaturation parameter of zooplankton; BFISH and FISH respectively represent fish filtration rate and fish biomass; and ZOOP represents the biomass of zooplankton.

For biochemical terms of DTP and DTN:

$$SK_3 = FMRP \cdot KD \cdot \tau_R \cdot CHLA + FMDP \cdot KM \cdot \tau_D \cdot CHLA + \quad (20)$$
$$RPJ \cdot \left(1 - \frac{DO}{DO + KTP}\right) \cdot \tau_{SP} + RPD \cdot SEDF -$$
$$ZDP \cdot CHLA \cdot \frac{DTP}{KTP + DTP} \cdot \tau_a - KPS \cdot DTP$$

$$SK_4 = FMRN \cdot KD \cdot \tau_R \cdot CHLA + FMDN \cdot KM \cdot \tau_D \cdot CHLA + \quad (21)$$
$$RNJ \cdot \left(1 - \frac{DO}{DO + KTN}\right) \cdot \tau_{SN} + RND \cdot SEDF -$$
$$ZDN \cdot CHLA \cdot \frac{DTN}{KTN + DTN} \cdot \tau_a - KNS \cdot DTN$$

where FMRP, FMRN, FMDP and FMDN are the phosphorus conversion rate of algae metabolite, the nitrogen conversion rate of metabolite, the phosphorus conversion rate of dead algae and the nitrogen conversion rate of dead algae respectively; KD and KM are metabolic rate and mortality of algae, respectively; RPJ and RNJ are the static release rates of phosphorus and nitrogen in sediments respectively; RPD and RND are the dynamic release rate of phosphorus and nitrogen in sediments respectively; SEDF is the flux of suspended substances at the water-soil interface; ZDP and ZDN are the absorption rate of phosphorus and nitrogen by algae respectively; KPS and KNS are sedimentation rates of DTP and DTN.

For biochemical terms of DO and BOD:

$$SK_5 = \tau_{ORE} \cdot KOD \cdot (DOSAT - DO) \cdot (1 + H_S) + \mu \cdot CHLA \cdot PP - \quad (22)$$
$$\tau_R \cdot KD \cdot CHLA \cdot ZHY + RO \cdot \tau_{SO} \cdot \frac{DO}{DO + KDO} - \tau_{KB} \cdot KB \cdot BOD$$

$$SK_6 = (\tau_{NP} \cdot ZHD + \tau_R \cdot ZHR)CHLA - \tau_{KB} \cdot KB \cdot BOD \quad (23)$$

where KOD is atmospheric reoxygenation rate; DOSAT is saturated DO; $H_s$ is characteristic wave height; PP is the photosynthetic oxygen production of algae; ZHY is respiratory oxygen consumption of algae; RO is the oxygen consumption of sediments; ZHD and ZHR are BOD production of algal death and metabolite; and KB is the degradation rate of BOD.

In said step (3), the 3D numerical model reads initialized data and boundary condition data at a certain time point from the database to improve computing speed and efficiency, and optimizes the model parameter combination by Monte Carlo method in accordance with the measured data in the previous simulation period to improve prediction precision of the model in this round of simulation; after completing the required data input, the model is automatically activated to carry out this round of simulation computations and returns the computation results of this round to the database; after ending the above process, the model enters into the dormant state and waits for the next round of simulation computations. Thus autonomous rolling forecasts can be achieved.

In said step (4), the algae bloom assessment algorithm functions to convert the abstract data into words or images that are easy for the public to understand, which helps to improve the warning efficiency. Based on the theoretical research related to algae blooms, the current assessment methods include expert scoring system, Carlson nutritional status index and probability of algae blooms, etc. Based on these methods, the algorithm program is programmed in the programming language and installed in the server. This program can automatically retrieve the latest comprehensive monitoring data and the model prediction data in the database, compute and analyze the data, generate an algae bloom risk map, and perform simple mathematical statistics on the risk map in a grid sampling manner, giving descriptive conclusions. These charts and conclusions are eventually published to the public via the network.

In said step (5), the predictive warning information on algae bloom of the lake is displayed on a public platform, said public platform can be an internet-based software platform, which uses relevant website to publish information, the website for publishing algae bloom information is an internet-based software platform, and a dialogue window for managing comprehensive monitoring and data mining system, and the information interaction between users and systems is realized through the website. The platform for publishing algae bloom information constructed by the invention can have the following functions: 1) providing practical algae bloom information; 2) being able to display real-time information of algae blooms obtained by the comprehensive monitoring system; 3) being able to display in combination of tables, maps and electronic maps; 4) being able to retrieve, count, and download historical data; 5) having 3D numerical models which can be manipulated by users; 6) having the production and publishing of cyanobacteria warning files which can be intervened by users; 7) automatically publishing the latest monitoring and predication information to relevant units and individuals in a variety of ways; 8) being able to draw contour maps and make simple Flash animation; and 9) having system management functions.

The advantages of the invention are as follows:

(1) The selection of monitoring indicators for algae blooms is scientific in that the invention is based on the research on the whole process of occurrence, development and termination of algae blooms, determines all indicators closely related to the process of algae blooms with a number of experiments and investigations, and analyzes the feasibility of techniques for acquiring each indicator.

(2) Real-time comprehensive monitoring of algae blooms is realized through the combination of remote sensing monitoring, automatic monitoring and manual monitoring. Wherein, the remote sensing monitoring can acquire the indicators of surface distribution, the automatic monitoring can acquire temporal continuous indicators at an extremely high frequency, and the manual monitoring can compensate for indicators which cannot be acquired by above two techniques.

(3) Automatic data receiving and preprocessing programs are developed. These programs can not only automatically store the collected data into the database, but also preprocess the raw data to eliminate abnormal data, or perform spatial-temporal interpolation on the missing data, such that the database not only stores the raw data, but also has a set of preprocessed spatial-temporal continuous data for further data mining.

(4) Using the self-designed 3D numerical model, with the simulation functions of the ecological processes closely related to the algae life process, such as nutrient salt circulation, sediment erosion and suspension and dissolved oxygen dynamics, and the computation results are more accurate.

(5) A secure, stable and intelligent data center is established. Dual-unit hot-standby mode, UPS power protection system and network hardware firewall technique of the data center can make the whole system always run safely and stably. In addition, the configuration of software such as database, data receiving and processing, 3D numerical model, parameter optimization programs and websites for publishing algae bloom information can not only automatically receive, process and mine comprehensive monitoring data, but also generate warning information and publish it to relevant units and individuals by Internet. Real-time receiving, rapid processing and timely publishing of algae bloom information are realized in this way.

(6) The 3D numerical simulation technique for algae blooms and assessment methods of algae bloom are seamlessly coupled to the comprehensive monitoring system. Although many algae bloom monitoring systems have been reported, these monitoring systems only implement data collection, and how to use the collected massive data still remains unknown. The invention implants a numerical model and an algae bloom assessment method into the data center, and seamlessly couples them with a comprehensive monitoring system, maximally extracts valuable information in the massive monitoring data through professional computation and analysis, and serves development of the social economy and production and life of residents.

The invention will be described in detail below in combination with specific examples. The scope of the invention is not limited to the specific embodiments but defined by the claims.

DETAILED DESCRIPTION OF THE PREFERRED EMBODIMENT

The invention will be further illustrated below in combination with brief description of the drawings and detailed description of the preferred embodiments. Examples below are for the purpose of illustrating the invention, rather than limiting the scope of the invention.

EXAMPLE 1

Taking Taihu Lake as an example, this Example further describes the method of the invention.

Figure 1:
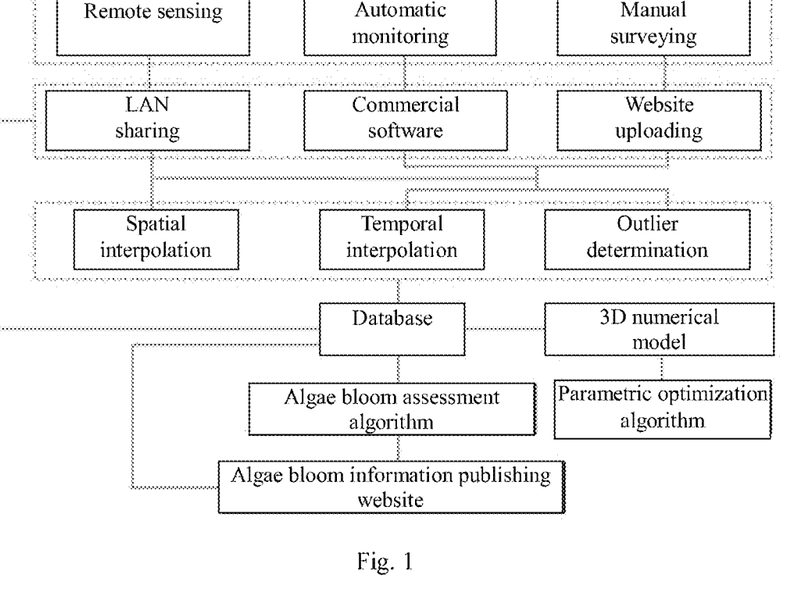
FIG. 1 is a flow diagram of the method of the invention.

FIG. 1 shows the flow diagram of the method of the invention, and the comprehensive monitoring and data mining method for algae bloom of lake of the invention comprises the steps as follows:

(1) Acquiring monitoring indicator data related to algae bloom of the lake to be monitored by three ways, i.e., remote sensing monitoring, automatic monitoring and manual surveying, wherein the monitoring indicator data comprise meteorological indicators, hydrological indicators, water-quality indicators and video images, and transmitting the acquired data to a data center by Internet;

Wherein, said remote sensing monitoring refers to a real-time monitoring by satellite remote sensing.

Said automatic monitoring refers to a monitoring network formed by a plurality of automatic monitoring stations via a wireless network to monitor the indicators to be monitored in a real-time manner.

Said manual surveying refers to a manual survey of the indicators.

Taihu Lake located in the Yangtze River Delta of China is the third largest freshwater lake in China and is now under threats of serious eutrophication and cyanobacteria blooms. The water crisis that occurred in Wuxi in 2007 caused huge losses to the production and life of people taking the Taihu Lake as the water source. According to the method described in step (1), on-site and laboratory comparison tests are performed on all indicators closely related to cyanobacteria blooms, and the development of relevant sensor techniques is fully investigated to give feasibility and precision of various indicators for the remote sensing monitoring, automatic monitoring and manual surveying, as shown in Table 1, and in order to minimize the manpower and improve the precision, the following measurement indicators are used to construct a monitoring indicator system for cyanobacteria bloom disasters of Taihu Lake, the indicators for remote sensing monitoring including effective wave height, water temperature, turbidity, transparency, chlorophyll a, area of water blooms, and intensity of water blooms; the indicators for automatic monitoring including wind speed, wind direction, atmospheric pressure, temperature, humidity, solar radiation and rainfall, 3D flow profile, water depth, effective wave height and period, water temperature, dissolved oxygen, turbidity, conductivity, redox potential, phycocyanobilin, chlorophyll and video image; and the indicators for manual surveying including concentrations of various nitrogen and phosphorus, chlorophyll a, phytoplankton, toxic and harmful substances, algal toxins and benthonic animals.

TABLE 1

Investigation of monitoring feasibility and precision of monitoring indicators for cyanobacteria bloom disasters of Taihu Lake

| Category | Indicator | Remote sensing | Automatic | Manual |
| --- | --- | --- | --- | --- |
| Meteorological parameters (feasibility/precision) | Wind speed | √/Medium | √/High | √/High |
| | Air temperature | √/Medium | √/High | √/High |
| | Solar radiation | | √/High | √/High |
| | Rainfall | | √/High | √/High |
| | Atmospheric pressure | | √/High | √/High |
| | Humidity | | √/High | √/High |

TABLE 1-continued

Investigation of monitoring feasibility and precision of monitoring
indicators for cyanobacteria bloom disasters of Taihu Lake

| Category | Indicator | Remote sensing | Automatic | Manual |
|---|---|---|---|---|
| Hydrological indicators (feasibility/precision) | 3D current speed | | √/High | √/High |
| | Water depth | | √/High | √/High |
| | Significant wave height | √/High | √/High | √/High |
| | Wave period | | √/High | √/High |
| Water quality parameters (feasibility/precision) | Water temperature | √/High | √/High | √/High |
| | DO | | √/High | √/High |
| | Turbidity | √/High | √/High | √/High |
| | Conductivity | | √/High | √/High |
| | Redox potential | | √/High | √/High |
| | Chla | √/Medium | √/Medium | √/High |
| | Phycocyanobilin | √/Low | √/Medium | √/High |
| | Suspended substance | √/High | √/High | √/High |
| | Transparency | √/Medium | √/High | √/High |
| | Concentrations of various nitrogen and phosphorus | | √/Medium | √/High |
| | COD and DOC | √/Medium | √/Medium | √/High |
| | Area of water blooms | √/High | | |
| | Intensity of water blooms | √/High | | |
| | Toxic and harmful substances | | | √/High |
| Biological indicators (feasibility/precision) | Algal toxins | | | √/High |
| | Number and viability of cells | | | √/High |
| | Phytoplankton communities | | | √/High |
| | Zooplankton and benthonic animals | | | √/High |
| Video images | Videos | | √/High | |

(2) After receiving the data, the data center performs data backup and data processing of the received data, checks the data missing and outliers, etc. and preprocesses the data by a self-programmed data preprocessing program, and said data preprocessing comprises the steps as follows:

Checking the data according to the set time interval for data acquisition, and performing data interpolation by a temporal interpolation if the data are interrupted; wherein said temporal interpolation method employs linear interpolation, spline function interpolation or piecewise interpolation. This Example employs the following method:

For linear interpolation of remote sensing, the algorithm is as follows:

For the data $a_1$ and $a_2$ in the data set, in the chronological order, the data $b_1, b_2, \ldots, b_n$ are missing there between, then:

$$b_i = \frac{(a_2 - a_1)*i}{n} + a_1 \quad (1)$$

where i=[1, n].

With the satellite inversion data involved, valid inversion results cannot be obtained in some areas for cloud coverage, in this case the spatial interpolation is used to fill the missing data in the cloud coverage area, and the spatial interpolation method employs the proximal point method, the Kriging method or the inverse distance weighted interpolation method; and in this Example, the inverse distance weighted interpolation method is used to implement the spatial interpolation. Assuming that the indicator values at the spatial point coordinates $(x_0, y_0)$ miss $C(x_0, y_0)$, a search radius is set such that there are at least 3 data points within the radius; then data of these known data points are used to obtain indicator values of unknown points:

$$C(x_0, y_0) = \frac{\frac{C(x_1, y_1)}{d_1} + \frac{C(x_2, y_2)}{d_2} + \ldots + \frac{C(x_n, y_n)}{d_n}}{\frac{1}{d_1} + \frac{1}{d_2} + \ldots + \frac{1}{d_n}} \quad (2)$$

Where, $C(x_1, y_1), C(x_2, y_2), \ldots, C(x_n, y_n)$ respectively represent the measured indicator values at the coordinate points in parentheses; $d_1, d_2, \ldots, d_n$ respectively represent the straight-line distances from the coordinate points in parentheses to the spatial point coordinates $(x_0, y_0)$, $n \geq 3$.

The basis for outlier determination and processing is trend test, expertise or numerical comparison, and the determined outlier is replaced with the data before the outlier; outlier determination and processing are performed on data by the 5× variance method in this Example, and the mean and variance of the $m^{th}$ measured datum $a_m$ and the five data before and after it are computed;

$$\bar{a} = 1/11 \Sigma_{n=1}^{11} a_n \quad (3)$$

$$SD^2 = 1/10 \Sigma_{n=1}^{11} (a_n - \bar{a})^2 \quad (4)$$

With $\bar{a} \pm 5$ SD as the judgment interval, the data satisfying $\bar{a} - 5\ SD \leq a_m \leq \bar{a} + 5\ SD$ are routine data, otherwise $a_m$ is replaced by the m−$1^{th}$ datum.

The preprocessed data are transmitted along with the raw data received by the data center to the database for storage.

The database of this Example is an Oracle database software, and the data of different sources have different data structures, and therefore are stored in the Oracle database by different storage strategies.

For single-point temporal continuous data, all data of a single monitoring station is stored in a single data sheet.

2D data are directly stored in the data sheet;

The data generated by the 3D numerical model are stored in the data sheet by time node.

Image or video data are stored in an array processor, and a data sheet is created in the database to record the path of image or video, the fields include number, time, and image/video path, and the image or video data are accessed in an indexed manner.

Figure 2:
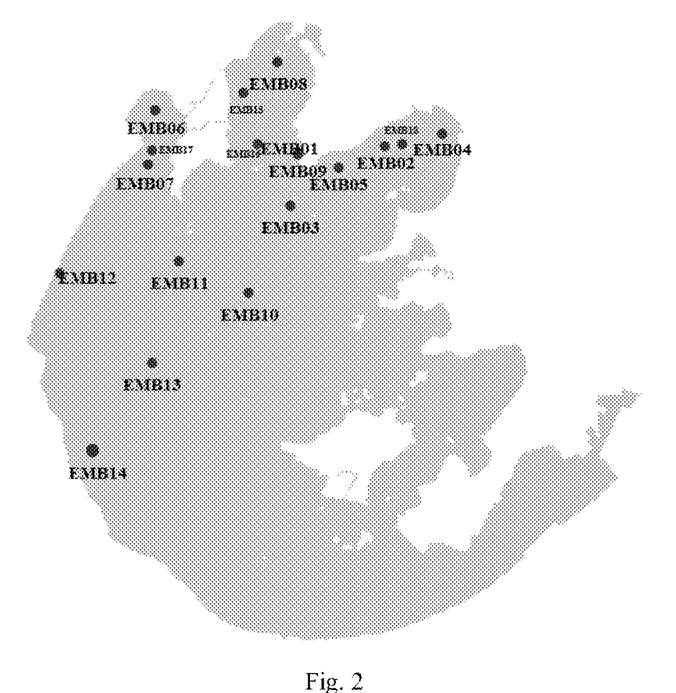
FIG. 2 is a distribution diagram of an automatic monitoring station of Example 1 of the invention.

In particular, for example, for single-point temporal continuous data of automatic monitoring and manual surveying, all data of a single station is stored in a single data sheet. The title of data sheet is the name of the monitoring station; the fields of the data sheet are the description of the indicator; the data are recorded as the measured data values stored in a chronological order. For example, the storage process of the water temperature, chlorophyll a and water depth of the automatic monitoring station EMB16 as shown in FIG. 2 is as follows: 1) a data sheet with a title of EMB16 is created first; 2) the fields of the sheet include number, time, water temperature, chlorophyll a and water depth, etc.; and 3) the first row of the sheet stores the first data recorded by EMB16.

The surface satellite remote sensing data are stored by two storage strategies: the satellite pictures are only stored under the path of image or video of the data sheet; the 2D data obtained by satellite picture inversion are directly stored in the data sheet. The satellite pictures are restored in the folder named "satellite picture" in the array processor. A data sheet is created in the database with a title of "satellite picture path"; the fields include number, time, picture path, and remark; each recording in the data sheet corresponds to a satellite picture acquired at a certain time. After satellite inversion, each pixel usually corresponds to one datum. For example, a satellite picture with a north-south span of 250*M and an east-west span of 250*N with a resolution of 250 m will generate an array having M rows and N columns after inversion of its water temperature indicator. Then, the array is stored as follows: creating a data sheet with a title of "inversed water temperature"; the fields include number, water layer, time, water temperature 1, water temperature 2, . . . , water temperature N; the first row of the sheet stores the data of the first, second, . . . , N columns in the first row of the array, the second row of the sheet stores the data of the first, second, . . . , N columns in the second row of the array, and so on, until the entire 2D array is stored; after completing the water temperature data inversed from the satellite picture at the first time point, the satellite inversion value of the second time point is stored, and so on, wherein, the water layer and time can mark satellite inversion data at different time points.

The data generated by the 3D numerical model are a 3D array. For example, the horizontal direction of the investigated lake is divided into M rows and N columns, and the water depth direction is divided into K layers, and for the simulated water temperature, it is TEMP(M,N,K). Similar to storage of the "inversion water temperature" data, the storage of the 3D array is the storage of K 2D arrays at one time point: the data sheet is titled as "simulated water temperature"; the fields include number, water layer, time, simulated water temperature 1, simulated water temperature 2, . . . , simulated water temperature N; each water layer is stored in the same manner as the inversed water temperature; after storage of 2D array of the first water layer is completed, the 2D numerical value of the second water layer is stored, and so on, until the 2D numerical value of the $K^{th}$ layer is stored. After storage of the 3D array at the first time point is completed, the 3D numerical value at the second time point is stored, and so on, wherein, the water layer and time can mark model-simulated data of the same water layer at different time points.

(3) Constructing a 3D numerical model of the lake to be monitored according to the data source stored in the database, as follows:

Constructing a hydrodynamic model of the lake to be monitored.

Superimposing a material migration and transformation model on the hydrodynamic model of the lake to be monitored, and performing equation coupling computation of the two models; wherein, said material migration and transformation model has such computation scalars as illumination, suspended substance, algae growth, nutrient salt circulation and dissolved oxygen.

Solving the model by the finite difference method to acquire simulation data of the numerical model.

In this Example, the self-constructed model is used, and the equation set describing the lake movement is as follows:

$$\frac{\partial Hu}{\partial x} + \frac{\partial Hv}{\partial y} + \frac{\partial Hw}{\partial \sigma} + \frac{\partial \xi}{\partial t} = 0 \tag{5}$$

$$\frac{\partial u}{\partial t} + u\frac{\partial u}{\partial x} + v\frac{\partial u}{\partial y} + w\frac{\partial u}{\partial \sigma} = \tag{6}$$
$$-fv - \frac{g\rho}{\rho_0}\frac{\partial \xi}{\partial x} + \frac{\partial}{\partial x}\left(A_h \frac{\partial u}{\partial x}\right) + \frac{\partial}{\partial y}\left(A_h \frac{\partial u}{\partial y}\right) + \frac{1}{H^2}\frac{\partial}{\partial \sigma}\left(A_v \frac{\partial u}{\partial \sigma}\right) + B_x$$

$$\frac{\partial v}{\partial t} + u\frac{\partial v}{\partial x} + v\frac{\partial v}{\partial y} + w\frac{\partial v}{\partial \sigma} = \tag{7}$$
$$-fu - \frac{g\rho}{\rho_0}\frac{\partial \xi}{\partial y} + \frac{\partial}{\partial x}\left(A_h \frac{\partial v}{\partial x}\right) + \frac{\partial}{\partial y}\left(A_h \frac{\partial v}{\partial y}\right) + \frac{1}{H^2}\frac{\partial}{\partial \sigma}\left(A_v \frac{\partial v}{\partial \sigma}\right) + B_y$$

$$\frac{1}{H}\left(\frac{\partial HT}{\partial t} + \frac{\partial HuT}{\partial x} + \frac{\partial HvT}{\partial y} + \frac{\partial HwT}{\partial \sigma}\right) = \tag{8}$$
$$\frac{\partial}{\partial x}\left(K_h \frac{\partial T}{\partial x}\right) + \frac{\partial}{\partial y}\left(K_h \frac{\partial T}{\partial y}\right) + \frac{1}{H^2}\frac{\partial}{\partial \sigma}\left(K_v \frac{\partial T}{\partial \sigma}\right) + \frac{S_h}{\rho C_P} + B_T$$

$$\rho(T) = 1000\left(1 - \frac{T + 288.9414}{508929.2(T + 68.12963)}(T - 3.9863)^2\right) \tag{9}$$

Where, u, v and w are respectively the flow rates in three directions x, y, and σ; H and t are water depth and time; g and ξ are gravitational acceleration (9.8 m/s) and water level (m); f is Coriolis force (=2Ω sin(φ)(u, v)), P is pressure, $B_x$, $B_y$, and $B_T$ are respectively the minor terms introduced by coordinate transformation of x-direction momentum, y-direction momentum and temperature equation; T is temperature; $K_h$ and $K_v$ are diffusion coefficients of heat in horizontal and vertical directions; $S_h$ is the heat entering the system from the outside; $C_p$ is the thermal capacity of water; $K_h$ and $K_v$ are the diffusion coefficients of heat in horizontal and vertical directions; ρ is water density, $\rho_0$ is water reference density; $A_h$ is horizontal eddy viscosity coefficient, which is 5 m2/s for Taihu Lake; $A_v$ is vertical eddy viscosity coefficient, which is defined by the formulas:

$$A_v = A_{v0}(1 + m_0 R_i)^{m_1} \tag{10}$$

$$A_{v0} = v_0 + \frac{l^2}{H}\sqrt{\left(\frac{\partial u}{\partial \sigma}\right)^2 + \left(\frac{\partial v}{\partial \sigma}\right)^2} \tag{11}$$

Where, $v_0$, $m_0$, $m_1$ values are respectively 5.0×10−6 m2/s, 0.1 and −1; l is Prandtl's length; $R_i$ is Richardson number, reflecting fluid stability condition, and its expression formula is:

$$R_i = -\frac{Hg}{\rho\left(\left(\frac{\partial u}{\partial \sigma}\right)^2 + \left(\frac{\partial v}{\partial \sigma}\right)^2\right)} \frac{\partial \rho}{\partial \sigma} \quad (12)$$

The wind energy input at the water-air interface with σ=1 and the friction resistance at the water-soil interface with σ=0 are expressed as:

$$\frac{\rho_s A_v}{H}\left(\frac{\partial u}{\partial \sigma}, \frac{\partial v}{\partial \sigma}\right) = (\tau_{Wx}, \tau_{Wx}) = \rho_a C_{WD}\sqrt{WS_x^2 + WS_y^2}\,(WS_x, WS_y) \quad (13)$$

$$\frac{A_v}{H}\left(\frac{\partial u}{\partial \sigma}, \frac{\partial v}{\partial \sigma}\right) = (\tau_{sx}, \tau_{sx}) = C_{SD}\sqrt{u^2 + v^2}\,(u, v) \quad (14)$$

Where, $\rho_a$ and $\rho_s$ represent air density and surface water density, respectively (=1000 kg/m and 1.3 kg/m); $C_{WD}$ is wind drag coefficient, which is 0.001, WS is wind speed (m/s) at 10 m above water meter; $C_{SD}$ is friction coefficient at the bottom of the lake, which is 0.003.

The hydrodynamic equations (5), (6) and (7) are solved by the splitting operator technique to generate the internal and external modes; then the internal and external modes are discretized by finite difference, wherein, the format of horizontal and temporal differences is explicit and the format of vertical difference is implicit, and the water surface displacement is subject to smoothing in temporal direction by a low-pass filter; and finally, the chasing method is used to solve the super-large sparse matrix. In this Example, the computational grid is set to divide the computational domain into 69×69 grids in a horizontal direction using a rectangular grid with a side length of 1000 m and into 5 layers in the vertical direction. The time step is 30 s.

On the basis of the above hydrodynamic model, the migration and transformation models of such scalars as illumination, suspended substance, algae growth, nutrient salt circulation and dissolved oxygen are superimposed:

$$\gamma_{PAR}(I, J, K) = \gamma_{0,PAR} + \gamma_{1,PAR}CHLA(I, J, K) + \gamma_{2,PAR}SED(I, J, K) \quad (15)$$

$$\frac{\partial S}{\partial t} + u\frac{\partial S}{\partial x} + v\frac{\partial S}{\partial y} + \left(w - \frac{w_s}{H}\right)\frac{\partial S}{\partial \sigma} = \quad (16)$$
$$B_S + \frac{\partial}{\partial x}\left(D_h\frac{\partial S}{\partial x}\right) + \frac{\partial}{\partial y}\left(D_h\frac{\partial S}{\partial y}\right) + \frac{1}{H^2}\frac{\partial}{\partial \sigma}\left(D_v\frac{\partial S}{\partial \sigma}\right) + \frac{J_0}{H}$$

$$\frac{\partial C_i}{\partial t} + u\frac{\partial C_i}{\partial x} + v\frac{\partial C_i}{\partial y} + w\frac{\partial C_i}{\partial \sigma} = \quad (17)$$
$$B_c + \frac{\partial}{\partial x}\left(D_h\frac{\partial C_i}{\partial x}\right) + \frac{\partial}{\partial y}\left(D_h\frac{\partial C_i}{\partial y}\right) + \frac{1}{H^2}\frac{\partial}{\partial \sigma}\left(D_v\frac{\partial C_i}{\partial \sigma}\right) + SK_i$$

Where, $\gamma_{PAR}(I, J, K)$ and $\gamma_{0,PAR}$ represent total attenuation coefficient and attenuation coefficient of pure water respectively; $\gamma_{1,PAR}$ and $\gamma_{2,PAR}$ represent specific attenuation coefficient of algae and specific attenuation coefficient of non-algae particulates; CHLA(I, J, K) is biomass of phytoplankton expressed by the concentration of chlorophyll a; SED(I, J, K) is the concentration of non-algae particulates; u, v and w are 3D the flow rates of new time step; S is the concentration of suspended substances; $w_s$ is the sedimentation rate of suspended substances; $J_0$ is the flux term at water-soil interface, including erosion flux and sedimentation flux; $C_i$ represents the concentration of the $i^{th}$ substance; $SK_i$ represents biochemical process items, with i=1, 2, 3, 4, 5, representing chlorophyll a, zooplankton (ZOOP), available phosphorus (DTP), available nitrogen (DTN), dissolved oxygen (DO), and five-day biochemical oxygen demand (BOD5.

Based on the computation results of the hydrodynamic model, the above equations are discretized by the finite difference method in a rectangular grid: the spatially discretizing is performed in upwind scheme; the format of horizontal and temporal differences is explicit and the format of vertical difference is implicit, and the chasing method is used to solve the super-large sparse matrix. The biochemical term involved in equation (17) is calculated by the following method.

For biochemical term of algae:

$$SK_1 = (\mu - \tau_{NP} \cdot KM)CHLA_{i,j,k} + \quad (18)$$
$$\frac{KS}{H\Delta Z}(CHLA_{i,j,k+1} - CHLA_{i,j,k})\tau_f - ZOOP_{i,j,k}ZP \cdot CHLA_{i,j,k} \cdot \tau_P$$

where μ is the total growth rate; KM is the non-predation mortality; KS is the floating rate; ZP is the filter feeding rate of zooplankton; CHLAi, j and k represent the biomass of phytoplankton in the i, j and k grids; $\tau_a$, $\tau_f$ and $\tau_p$ here as well as $\tau_{ZP}$, $\tau_{KB}$, $\tau_s$, $\tau_d$ and $\tau_{so}$ involved in the formula below are all temperature influence factors, and their expression formulae are $\theta_a^{T-20}$, $\theta_f^{T-20}$, $\theta_p^{T-20}$, $\theta_{ZP}^{T-20}$, $\theta_{KB}^{T-20}$, $\theta_s^{T-20}$, $\theta_d^{T-20}$ and $\theta_{so}^{T-20}$ respectively, wherein $\theta_a$, $\theta_p$, $\theta_{ZP}$, $\theta_{KB}$, $\theta_s$, $\theta_d$ and $\theta_{so}$ are temperature multipliers.

For biochemical term of zooplankton:

$$SK_2 = \left(\mu_{ZP} \cdot ZOOP \cdot \frac{CHLP}{KCHLA + CHLA} - BFISH \cdot FISH\right) \cdot \tau_{ZP} \quad (19)$$

where $\mu_{zp}$ is the growth rate of zooplankton; KCHLA is the predation semisaturation parameter of zooplankton; BFISH and FISH respectively represent fish filtration rate and fish biomass; and ZOOP represents the biomass of zooplankton.

For biochemical terms of DTP and DTN:

$$SK_3 = FMRP \cdot KD \cdot \tau_R \cdot CHLA + FMDP \cdot KM \cdot \tau_D \cdot CHLA + \quad (20)$$
$$RPJ \cdot \left(1 - \frac{DO}{DO + KTP}\right) \cdot \tau_{SP} + RPD \cdot SEDF -$$
$$ZDP \cdot CHLA \cdot \frac{DTP}{KTP + DTP} \cdot \tau_a - KPS \cdot DTP$$

$$SK_4 = FMRN \cdot KD \cdot \tau_R \cdot CHLA + FMDN \cdot KM \cdot \tau_D \cdot CHLA + \quad (21)$$
$$RNJ \cdot \left(1 - \frac{DO}{DO + KTN}\right) \cdot \tau_{SN} + RND \cdot SEDF -$$
$$ZDN \cdot CHLA \cdot \frac{DTN}{KTN + DTN} \cdot \tau_a - KNS \cdot DTN$$

where FMRP, FMRN, FMDP and FMDN are the phosphorus conversion rate of algae metabolite, the nitrogen conversion rate of metabolite, the phosphorus conversion rate of dead algae and the nitrogen conversion rate of dead algae respectively; KD and KM are metabolic rate and mortality of algae, respectively; RPJ and RND are the static release rates of phosphorus and nitrogen in sediments respectively; RPD and RND are the dynamic release rate of phosphorus and nitrogen in sediments respectively; SEDF is the flux of suspended substances at the water-soil interface; ZDP and ZDN are the absorption rate of phosphorus and nitrogen by algae respectively; KPS and KNS are sedimentation rates of DTP and DTN.

For biochemical terms of DO and BOD:

$$SK_5 = \tau_{ORE} \cdot KOD \cdot (DOSAT - DO) \cdot (1 - H_s) + \mu \cdot CHLA \cdot PP - \tau_R \cdot KD \cdot CHLA \cdot ZHY + RO \cdot \tau_{SO} \cdot \frac{DO}{DO + KDO} - \tau_{KB} \cdot KB \cdot BOD \quad (22)$$

$$SK_6 = (\tau_{NP} \cdot ZHD + \tau_R \cdot ZHR)CHLA - \tau_{KB} \cdot KB \cdot BOD \quad (23)$$

where KOD is atmospheric reoxygenation rate; DOSAT is saturated DO; $H_s$ is characteristic wave height; PP is the photosynthetic oxygen production of algae; ZHY is respiratory oxygen consumption of algae; RO is the oxygen consumption of sediments; ZHD and ZHR are BOD production of algal death and metabolite; and KB is the degradation rate of BOD.

The 3D numerical model reads initialized data and boundary condition data at a certain time point from the database, and optimizes the model parameter combination by Monte Carlo method in accordance with the measured data in the previous simulation period; after completing the required data input, the model is automatically activated to carry out this round of simulation computations and returns the computation results of this round to the database; after ending the above process, the model enters into the dormant state and waits for the next round of simulation computations.

Figure 3:
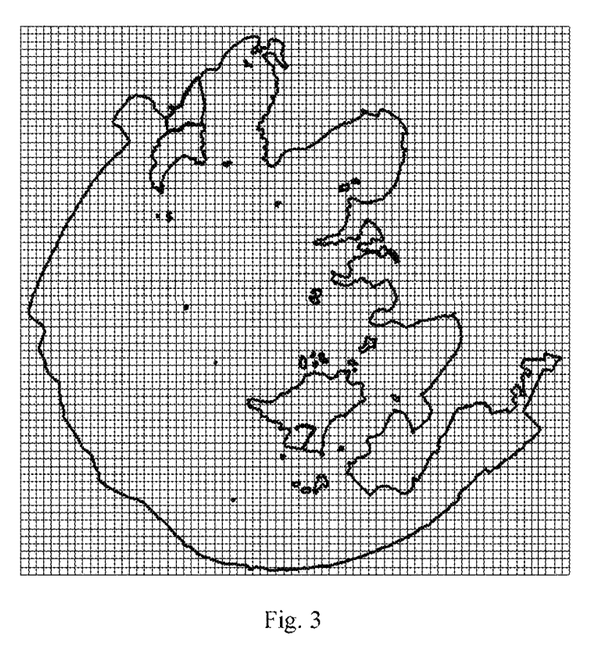
FIG. 3 is a division diagram of a numerical computation grid of a model of Example 1 of the invention.

In summary of this Example, the computing of 3D numerical model for the cyanobacteria blooms of Taihu Lake adopts a rectangular grid. According to on-site measurement of the topography of the water area prone to cyanobacteria blooms in Taihu Lake, the whole lake is divided into 4,900 computational grids including land and water in the horizontal plane, as shown in FIG. 3. Based on this grid map, the model reads the measured values of lake wave, lake current, water temperature, illumination, chlorophyll a, nutrient salt, dissolved oxygen and organic substance from the Oracle database at 12:00 on the forecast day, and uses the inverse distance weighted interpolation method to interpolate these data into the 4,900 computational grids (the value in the land grids is set to −9999) as the initial concentration field for this round of forecasting. At the same time, based on the measured water environment data during the previous forecasting period (3d), the model parameters of this forecasting period are optimized, and the Monte Carlo method is used to optimize the model parameters. After the initialization and parameter optimization are completed, it needs to acquire the weather condition of this forecasting period 3d. The wind speed, wind direction, temperature, radiation, rainfall, atmospheric pressure and relative humidity required for the model for the future 3 days are calculated by a weather observation and forecasting model (WRF). Finally, the model is automatically activated to simulate and predict changes of lake wave, lake current, water temperature, illumination, chlorophyll a, nutrient salt, dissolved oxygen and organic substance in future 3 days, and transmits the generated 3D array back to the Oracle database.

(4) Assessing the risk of algae bloom of the lake to be monitored according to the simulation data of the numerical model.

The algae bloom assessment algorithm functions to convert the abstract data into words or images that are easy for the public to understand. In this Example, the risk assessment algorithm of cyanobacteria blooms of Taihu Lake utilizes Intel Visual Fortran and Microsoft Visual Studio to develop an assessment algorithm program, which can automatically read simulation data of 3D numerical model from a database and assess the risk of cyanobacteria blooms in future 3 days. Assessment results are published on website.

The risk assessment algorithm of cyanobacteria blooms of Taihu Lake based on the expert assessment system is performed in accordance with the spatial distribution of changes of lake wave, lake current, water temperature, illumination, chlorophyll a, nutrient salt, dissolved oxygen and organic substance in future 3 days which are simulated by the 3D numerical model, introduces expert scoring, determines the risk level of cyanobacteria blooms in different locations at different time in Taihu Lake, and characterizes the risk levels in different colors. It is implemented as follows:

(1) Taihu Lake is divided into functional water areas. The principle of division based on the similarity of natural conditions, the similarity of lake pollution status, the similarity of targets of use, and integrity of administrative management, takes indicators of the natural conditions (water depth, properties of lake current, organism), water pollution indicators (TP, TN, CODMn, organic pollutant), indicators of the targets of use (drinking, fishing, tourism, nature reserves) and administrative divisions as an indicator system to perform the functional division of water areas.

(2) The indicator system and classification system for risk assessment of algae blooms are established, based on the principles of scientificity, representativeness, quantifiability and accessibility, the ecological risk of algae blooms is divided into three levels according to their importance, i.e., key indicators, important indicators and general indicators.

(3) According to the expertise, the indicators of different water units and water environments are assigned with different weights, and then the ecological risk scores of algae blooms are computed according to the following formula:

$$G = \sum_{i=1}^{n} Y_i \cdot W_i \cdot C_i \quad (24)$$

where $Y_i$ is the score of the indicator i; $W_i$ is the weight of the indicator i, $C_i$ is the weight of the water unit, and G is the comprehensive score. According to the computation result and expertise, different risk levels of algae blooms in various functional water areas are indicated in different colors, including extremely severe disaster, severe disaster, moderate disaster, light disaster, and no disaster, etc. For specific implementation method of the assessment algorithm, see literature of Liu Jutao et al. (Study on risk assessment method of cyanobacteria blooms in Taihu Lake, China Environmental Science, 2011, 31(3): 498-503), which is not detailed in the present invention.

(5) Displaying predictive warning information on algae bloom of the lake on a public platform.

The predictive warning information on algae bloom of the lake is displayed on a public platform, said public platform can be an internet-based software platform, which uses are relevant website to publish information, the website for publishing algae bloom information is an internet-based software platform, and a dialogue window for managing comprehensive monitoring and data mining systems, and the information interaction between users and systems is realized through the website. The website for publishing algae bloom information constructed in this Example is an Internet-based software platform, and a dialogue window for managing comprehensive monitoring and data mining system, and information interaction between users and systems is realized through website, with the main functions including Home, telemetric data, surveyed data, satellite data, predictive warning, user center and other functions.

The comprehensive monitoring display is implemented in three web pages of telemetric data, surveyed data and satellite data, and their respective page functions are similar. The comprehensive monitoring web page interacts with the database to display the real-time environment information of the lake collected by the comprehensive monitoring system of Taihu Lake to the public. The main loading controls and reference objects include database engine, buttons, charts, check boxes, drop-down combo boxes, text boxes, time and WebGIS, etc. First, the web page can display real-time meteorological, hydrological, and water quality monitoring data of a single site on an electronic map, or display the surface monitoring data through a secondary development gridding of the electronic map. Secondly, the web page can also provide historical data retrieval, downloading and simple statistical analysis services for users with different permissions. Data retrieval and downloading refer to that users provide the information such as site, indicator and time, the website automatically generates SQL sentences to send commands to the database, the database receives the commands and returns the corresponding data sets, displays the data to the users in forms of graphs and tables, and can generate files in specified formats for users to download. For simple statistical analysis, the web site provides statistical analysis of time series of no more than 1 year, including simple statistical functions such as maximum, minimum, average, counting and summation, etc.

The predictive warning web page interacts with the database to display the predictive warning information of algae blooms of Taihu Lake, and the main loading controls and reference objects include database engine, time, button, iWebOffice, text boxes, drop-down list boxes, check boxes, Frame, WebGIS and Flash, etc. The web page will: 1) display information such as computational grids, time steps, forecast period, initial values, and boundary conditions involved in the 3D numerical model in the form of a web page sheet, and also list information such as all model parameter names, functions, value ranges and current values. At the same time, the users can modify the above model settings through a built-in iWebOffice plug-in; 2) draw contour maps. The web page can retrieve the simulation data of the model, draw the contour maps through WebGIS, and play these contour maps in the Flash control in chronological order to form an animation of the temporal and spatial changes of the simulated environment indicators of Taihu Lake in future 3 days; 3) automatically produce a half-week monitoring and warning report on water pollution and cyanobacteria of Taihu Lake in the pre-specified format. In addition to displaying on the web page, the half-week report can also be downloaded via a hyperlink or automatically sent to a specified email address at a specified time.

The web page of the user center mainly functions to manage users of different levels and publish news by users themselves, and the main loading controls and reference objects include database engine, buttons, Flash, pictures and sheets, etc. First, the web page can set different permissions for all users, including system administrators, advanced users, intermediate users and novice users. The system administrator has all the permissions of the website and can make all the rules. Advanced users can browse all pages of the website, access the database, download monitoring data in batches, publish news and manipulate 3D numerical models. Intermediate users can browse all pages of the website, access the database, and download monitoring data in batches. Novice users are general visitors and can only browse the algae bloom information displayed by the web site to the public.

EXAMPLE 2

Taking Taihu Lake as an example, this Example further describes the system of the invention.

The comprehensive monitoring and data mining system for algae bloom of lake of the invention comprises a monitoring system and a data processing system, said monitoring system is used for acquiring data to be monitored; said monitoring system comprises a remote sensing monitoring system for monitoring by remote sensing, an automatic monitoring system for monitoring by automatic monitoring and a manual surveying system for manual acquisition of data to be monitored.

Remote sensing monitoring system comprises a satellite data receiving antenna, a computer and a power supply system, wherein, said power supply system is used to supply power for power consuming devices, the satellite data receiving antenna receives satellite data and transmits them to the computer, the data are subject to remote sensing inversion by the computer and the processed data are transmitted to the data processing system by Internet.

Automatic monitoring system is a monitoring network formed by a plurality of automatic monitoring stations via wireless network, and a single automatic monitoring station consists of a water surface supporting system, a power supply system, a safety warning system and a data acquisition system; said water surface supporting system is a bearing structure for hardware devices of the automatic monitoring station; said power supply system is used to supply power for power consuming devices of the automatic monitoring station; said safety warning system is used for safety warning and preventing the automatic monitoring station from accidental damages; and said data acquisition system is used to acquire data to be monitored from a meteorological instrument, a hydrological instrument, a water-quality instrument and a video instrument and transmit the acquired data to the data processing system via wireless network.

Manual surveying system acquires data manually and transmits the data to the data processing system by Internet.

Data processing system is used to receive and process the data acquired by the monitoring system; the data processing system comprises a server, an array processor, a computer, a computing workstation, a hardware firewall, a router, network cables and a power supply device; the server adopts a dual-unit hot-standby mode, two servers and the array processor for data storage realize heartbeat connection through a three-prong cable, all computers, servers, and computing workstations are connected to the hardware firewall through a network cable, and the hardware firewall is communicated to the external network through the router.

After receiving the data, the data processing system performs data backup and data processing of the received data, including data preprocessing, 3D numerical simulation and algae bloom assessment, and acquires predictive indicators and risk assessments of algae bloom of the lake, and publishes them through a public platform. Said data preprocessing, 3D numerical simulation and assessment algorithm of algae blooms can refer to the algorithm used in Example 1.

As shown in FIG. 2, the automatic monitoring station in this Example refers to a monitoring network consisting of 18 automatic monitoring stations distributed in areas with serious cyanobacteria blooms in Taihu Lake. Water environment information of the water areas where the 18 automatic monitoring stations are located can be continuously recorded in a real-time manner with a time resolution of 30 minutes.

Said power supply device supplies power by a UPS system, and said two servers are located in a local area network under a hardware firewall and a router, and in the same local area network, there is a computer for receiving and processing remote sensing data and a computing workstation for operating 3D numerical model. The computing workstation is in the same local area network as the two servers, thus the 3D numerical model can automatically and fast read the data in the database, and can return the computation results to the Oracle database. All the devices are connected with the UPS system via cables, the UPS system is connected with civil AC, and the UPS system provides a stable power supply for the data center.

Satellite data of a computer in the same local area network are transmitted to the server by programming a remote sensing data receiving program, and stored in the array processor in a designated file naming pattern. The communication modules of the automatic monitoring station include a GRPS module and a CR1000 data collector. Only if a lognet software matching CR1000 is installed on the server side, the monitoring data can be automatically transmitted to the server side and stored in the array processor in a designated file naming pattern.

The invention claimed is:

1. A comprehensive monitoring and data mining method for algae bloom in a lake, comprising:
   (1) acquiring monitoring indicator data related to algae bloom of the lake to be monitored by remote sensing monitoring, automatic monitoring and manual surveying, the monitoring indicator data comprising meteorological indicators, hydrological indicators, water-quality indicators and video images, and transmitting the acquired monitoring indicator data to a data center by Internet wherein said remote sensing monitoring refers to a real-time monitoring by satellite remote sensing; wherein automatic monitoring refers to a monitoring network formed by a plurality of automatic monitoring stations connected via a wireless network to monitor the meteorological indicators, hydrological indicators, water-quality indicators and video images to be monitored in a real-time manner; wherein manual surveying refers to a manual survey of water-quality indicators including total nitrogen, total dissolved nitrogen, ammonia nitrogen, nitrate nitrogen, nitrite nitrogen, total phosphorus, total dissolved phosphorus, orthophosphate and cyanobacteria-derived pollutants;
   (2) performing data backup and data preprocessing of the received monitoring indicator data in the data center, wherein, said data preprocessing includes:
   checking the monitoring indicator data according to a set time interval for data acquisition to detect a data interruption leading to missing monitoring indicator data, and, in response to the data interruption, to perform a data interpolation of the monitoring indicator data by a temporal interpolation;
   filling missing monitoring indicator data of a cloud coverage area by a spatial interpolation for satellite data acquired by the remote sensing monitoring;
   performing an outlier determination to determine an outlier as abnormal monitoring indicator data and processing of the monitoring indicator data, and replacing the abnormal monitoring indicator data with the monitoring indicator data before the determined outlier;
   transmitting the preprocessed monitoring indicator data along with the acquired monitoring indicator data received by the data center to a database for storage;
   (3) constructing a 3D numerical model of the lake to be monitored according to the preprocessed monitoring indicator data and the acquired monitoring indicator data stored in the database, as follows:
   constructing a hydrodynamic model of the lake to be monitored;
   superimposing a material migration and transformation model on the hydrodynamic model of the lake to be monitored, and performing equation coupling computation of the two models; wherein, said material migration and transformation model including computation scalars comprising illumination, suspended substance, algae growth, nutrient salt circulation and dissolved oxygen;
   solving the 3D numerical model by a finite difference method to acquire simulation data of the 3D numerical model;
   (4) assessing a risk of algae bloom of the lake to be monitored according to the simulation data of the 3D numerical model; and
   (5) displaying predictive warning information on algae bloom of the lake on a public platform.

2. The method according to claim 1, wherein in said step (2), the preprocessed monitoring indicator data and the acquired monitoring indicator data are classified and stored in the database as follows:
   for single-point temporal continuous data, all data of a single monitoring station are stored in a data sheet;
   2D data are directly stored in the data sheet;
   the data generated by the 3D numerical model are stored in the data sheet by time node;
   image or video data are stored in an array processor, and a data sheet is created in the database to record a path of an image or video, fields of the data sheet include number, time, and image/video path, and the image or video data are accessed in an indexed manner.

3. The method according to claim 1, wherein in said step (2), the database is constructed for multi-source heterogeneous data sets using a database software.

4. The method according to claim 1, wherein in said step (2), said temporal interpolation method employs one of linear interpolation, spline function interpolation and piecewise interpolation;
   a spatial interpolation method employs one of a proximal point method, the Kriging method and an inverse distance weighted interpolation method; and
   outlier determination and processing are based on one of trend test and numerical comparison.

5. The method according to claim 1, wherein in said step (2), said temporal interpolation method employs the linear interpolation method as follows:

for data a1 and a2 in the data set, in chronological order, the data b1, b2, . . . , bn are missing there between, then:

$$b_i = \frac{(a_2 - a_1) * i}{n} + a_1 \quad (1)$$

where i=[1, n].

6. The method according to claim 1, wherein in said step (2), said spatial interpolation method employs an inverse distance weighted interpolation method as follows:
with indicator values at spatial point coordinates (x0, y0) miss C(x0, y0), setting a search radius such that there are at least three data points within the search radius; then the data of these known data points are used to obtain indicator values of unknown points:

$$C(x_0, y_0) = \frac{\frac{C(x_1, y_1)}{d_1} + \frac{C(x_2, y_2)}{d_2} + \ldots + \frac{C(x_n, y_n)}{d_n}}{\frac{1}{d_1} + \frac{1}{d_2} + \ldots + \frac{1}{d_n}} \quad (2)$$

where $C(x_1, y_1)$, $C(x_2, y_2)$, . . . , $C(x_n, y_n)$ respectively represent the measured indicator values at the coordinate points in parentheses; $d_1, d_2, \ldots, d_n$ respectively represent straight-line distances from the coordinate points in parentheses to the spatial point coordinates $(x_0, y_0)$, n≥3.

7. The method according to claim 1, wherein in said step (2), the outlier determination is performed by the 5× variance method as follows: computing the mean and variance of the $m^{th}$ measured datum $a_m$ and the five data before and after it:

$$\bar{a} = \frac{1}{11}\Sigma_{n=1}^{11} a_n \quad (3)$$

$$SD^2 = \frac{1}{10}\Sigma_{n=1}^{11}(a_n - \bar{a})^2 \quad (4)$$

with $\bar{a} \pm 5$ SD as a judgment interval, the data satisfying $\bar{a} - 5\ SD \leq a_m \leq \bar{a} + 5\ SD$ are routine data, otherwise $a_m$ is replaced by the m−1$^{th}$ datum.

8. The method according to claim 1, wherein in said step (3), a control equation of the hydrodynamic model is as follows:

$$\frac{\partial Hu}{\partial x} + \frac{\partial Hv}{\partial y} + \frac{\partial Hw}{\partial \sigma} + \frac{\partial \xi}{\partial t} = 0 \quad (5)$$

$$\frac{\partial u}{\partial t} + u\frac{\partial u}{\partial x} + v\frac{\partial u}{\partial y} + w\frac{\partial u}{\partial \sigma} = \quad (6)$$

$$-fv - \frac{g\rho}{\rho_0}\frac{\partial \xi}{\partial x} + \frac{\partial}{\partial x}\left(A_h \frac{\partial u}{\partial x}\right) + \frac{\partial}{\partial y}\left(A_h \frac{\partial u}{\partial y}\right) + \frac{1}{H^2}\frac{\partial}{\partial \sigma}\left(A_v \frac{\partial u}{\partial \sigma}\right) + B_x$$

$$\frac{\partial v}{\partial t} + u\frac{\partial v}{\partial x} + v\frac{\partial v}{\partial y} + w\frac{\partial v}{\partial \sigma} = \quad (7)$$

$$-fu - \frac{g\rho}{\rho_0}\frac{\partial \xi}{\partial y} + \frac{\partial}{\partial x}\left(A_h \frac{\partial v}{\partial x}\right) + \frac{\partial}{\partial y}\left(A_h \frac{\partial v}{\partial y}\right) + \frac{1}{H^2}\frac{\partial}{\partial \sigma}\left(A_v \frac{\partial v}{\partial \sigma}\right) + B_y$$

$$\frac{1}{H}\left(\frac{\partial HT}{\partial t} + \frac{\partial HuT}{\partial x} + \frac{\partial HvT}{\partial y} + \frac{\partial HwT}{\partial \sigma}\right) = \quad (8)$$

$$\frac{\partial}{\partial x}\left(K_h \frac{\partial T}{\partial x}\right) + \frac{\partial}{\partial y}\left(K_h \frac{\partial T}{\partial y}\right) + \frac{1}{H^2}\frac{\partial}{\partial \sigma}\left(K_v \frac{\partial T}{\partial \sigma}\right) + \frac{S_h}{\rho C_P} + B_T$$

$$\rho(T) = 1000\left(1 - \frac{T + 288.9414}{508929.2(T + 68.12963)}(T - 3.9863)^2\right) \quad (9)$$

where u, v and w are respectively flow rates in three directions x, y, and σ; H and t are water depth and time; g and ξ are gravitational acceleration and water level; f is Coriolis force, P is pressure, $B_x$, $B_y$, and $B_T$ are respectively minor terms introduced by coordinate transformation of x-direction momentum, y-direction momentum and temperature equation; T is temperature; $S_h$ is heat entering the system from the outside; $C_p$ is thermal capacity of water; $K_h$ and $K_v$ are diffusion coefficients of heat in horizontal and vertical directions; ρ is water density, $\rho_0$ is water reference density; $A_h$ is horizontal eddy viscosity coefficient; $A_v$ is vertical eddy viscosity coefficient, which is defined by the formulas:

$$A_v = A_{v0}(1 + m_0 R_i)^{m_1} \quad (10)$$

$$A_{v0} = v_0 + \frac{l^2}{H}\sqrt{\left(\frac{\partial u}{\partial \sigma}\right)^2 + \left(\frac{\partial v}{\partial \sigma}\right)^2} \quad (11)$$

where $v_0$, $m_0$, $m_1$ values are respectively 5.0×10−6 m2/s, 0.1 and −1; l is Prandtl's length; $R_i$ is Richardson number, reflecting fluid stability condition, and its expression formula is:

$$R_i = -\frac{Hg}{\rho\left(\left(\frac{\partial u}{\partial \sigma}\right)^2 + \left(\frac{\partial v}{\partial \sigma}\right)^2\right)}\frac{\partial \rho}{\partial \sigma} \quad (12)$$

wind energy input at the water-air interface with σ=1 and the friction resistance at the water-soil interface with σ=0 are expressed as:

$$\frac{\rho_s A_v}{H}\left(\frac{\partial u}{\partial \sigma}, \frac{\partial v}{\partial \sigma}\right) = (\tau_{Wx}, \tau_{Wx}) = \rho_a C_{WD}\sqrt{WS_x^2 + WS_y^2}\,(WS_x, WS_y) \quad (13)$$

$$\frac{A_v}{H}\left(\frac{\partial u}{\partial \sigma}, \frac{\partial v}{\partial \sigma}\right) = (\tau_{sx}, \tau_{sx}) = C_{SD}\sqrt{u^2 + v^2}\,(u, v) \quad (14)$$

where $\rho_a$ and $\rho_s$ represent air density and surface water density, respectively; $C_{WD}$ is wind drag coefficient; WS is wind speed at 10 m above water meter; $C_{SD}$ is friction coefficient at the bottom of the lake;
wherein hydrodynamic equations (5), (6) and (7) are solved by splitting operator technique to generate internal and external modes; then the internal and external modes are discretized by finite difference, wherein, a format of horizontal and temporal differences is explicit and a format of vertical difference is implicit, and water surface displacement is subject to smoothing in temporal direction by a low-pass filter; and a chasing method is used to solve the super-large sparse matrix.

9. The method according to claim 1, wherein in said step (3), the 3D numerical model reads initialized data and boundary condition data at a certain time point from the database, and optimizes the model parameter combination by Monte Carlo method in accordance with the measured data in the previous simulation period;
after completing the required data input, the model is automatically activated to carry out this round of simulation computations and returns the computation results of this round to the database;

after ending the above process, the model enters into a dormant state and waits for the next round of simulation computations.

\* \* \* \* \*